Figure 2:
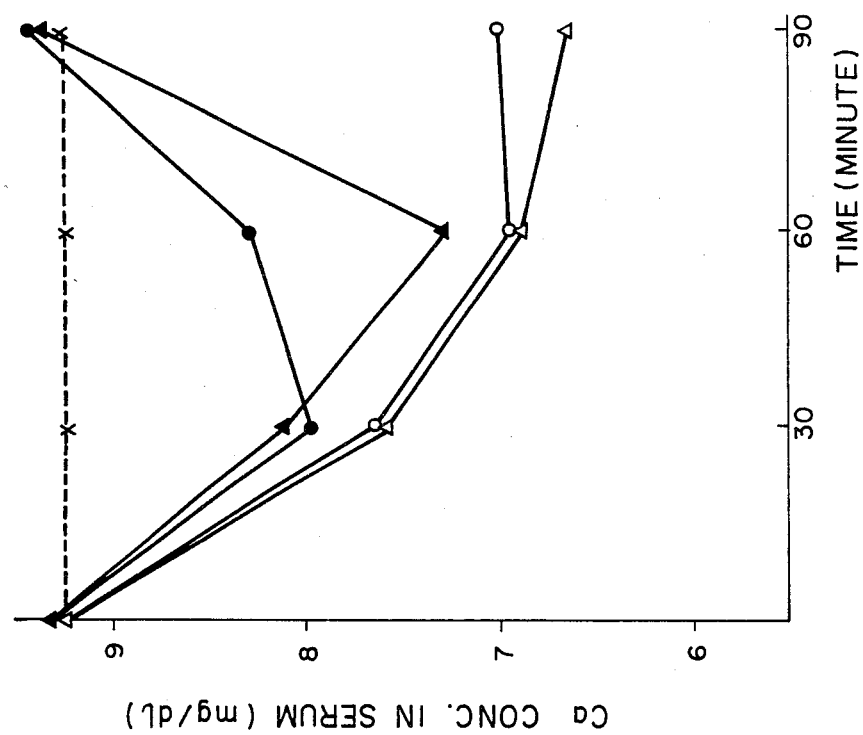

United States Patent [19]

Morishita et al.

[11] Patent Number: 4,609,640

[45] Date of Patent: Sep. 2, 1986

[54] PREPARATION HAVING EXCELLENT ABSORPTION PROPERTY

[75] Inventors: Masataka Morishita; Renji Aikawa; Yoshiaki Yamamoto, all of Shizuoka, Japan

[73] Assignee: Toyo Jozo Company, Ltd., Japan

[21] Appl. No.: 342,080

[22] Filed: Jan. 25, 1982

[30] Foreign Application Priority Data

Nov. 17, 1981 [JP] Japan .................. 56-184861

[51] Int. Cl.$^4$ ............................ C07K 7/10; C07K 7/36
[52] U.S. Cl. ....................................... 514/12; 530/300; 530/350
[58] Field of Search ..................... 260/112.5, 112.5 T; 424/177

[56] References Cited

U.S. PATENT DOCUMENTS 4,166,847 9/1979 Mitsui ................................. 424/180
4,241,051 12/1980 Christie et al. ............... 260/112.5 T

OTHER PUBLICATIONS

Keltz et al., *American Journal of Chemical Nutrition*, 31, 1167–1171 (1978).

*Primary Examiner*—Delbert R. Phillips
*Assistant Examiner*—F. T. Moezie
*Attorney, Agent, or Firm*—Wyatt, Gerber, Shoup, Scobey and Badie

[57] ABSTRACT

A preparation containing an absorption promoter selected from specific classes of water-soluble macromolecular compounds having chelating activity, preferably in the presence of a salt at a concentration such that the composition exhibits higher osmotic pressure than isotonic sodium chloride solution, and a medicine is found to promote absorption of the medicine through a gastrointestinal organ such as the colon, rectum, or vagina.

16 Claims, 2 Drawing Figures

PREPARATION HAVING EXCELLENT ABSORPTION PROPERTY

This invention relates to novel preparations having excellent absorption properties which are useful to improve the absorption of a medicine poor in absorption property through the rectum or other organs in a body by administration of such a medicine into rectum or other openings in an aqueous composition with sufficient water-soluble so that the composition exhibits higher osmotic pressure than isotonic sodium chloride solution and a water-soluble macromolecular compound having chelating action. Further, it also pertains to a preparation having good absorption property comprising a water-soluble macromolecular compound having chelating activity and a medicine, which can improve absorption property to a great extent of a medicine, which is itself poor in absorption property, and also maintain a high concentration thereof in blood for a long time.

Absorption of a medicine through a digestive organ, irrespective of whether it may be stomach, small intestine, large intestine, rectum or mouth, has heretofore been generally believed to proceed according to pH Partition theory (Modern Pharmaceutics, Marcel Dekker, Inc., p. 31–49). Hence, a medicine readily dissociated in the respective organs at the absorption sites or a medicine having poor lipophilicity tends to be poorly absorbed. Such difficultly absorptive medicines are administered as injections under the present circumstances. For improvement of absorption property of a medicine, there have been made various investigations such as Prodrug, Sofdrug, utilization of ion pairs or complex formation. But none of these proposals is effective specifically for individual medicines, and no universally applicable method is known in the art ("Pharmaceutics" written by Nogami).

It has now been discovered that in the mechanism of membrane absorption through digestive or other organs, which is believed to proceed according to the pH Partition theory as mentioned above, a water-soluble macromolecular compound having a chelating action capable of bonding at least calcium ions or magnesium ions causes a change in membrance permeability, whereby membrance absorption of a medicine can be improved to promote successfully absorption thereof. Further, it has also been found that membrane absorption can be markedly improved by addition of a water-soluble substance at a concentration such that the resulting aqueous composition exhibits higher osmotic pressure than isotonic sodium chloride solution so that the resulting preparation has higher tonicity than the osmotic pressure of a body fluid. It has further been found that a suppository containing a selected therapeutic agent prepared in accordance with this invention may be inserted into rectum or vagina and the agent will be excellently absorbed through membranes and maintain a high concentration in the blood for a long time. The medicines to be used in the present invention are very broad. In particular, so called water-soluble medicines having good solubility in water, for example, those with partition coefficients of up to 50 in chloroform/water or medicines readily dissociated into ions, are useful. Further, medicines applicable only as injections in the prior art are also found to be made excellently absorbable easily as preparations such as suppositories. Even a medicine with a high molecular weight such as polypeptide hormones is also found as the result of this invention to be made efficiently absorbable in the form of a preparation such as suppository.

The present invention has been accomplished based on the above findings, and the object of the present invention is to provide a good preparation from which the absorption of a medicine can be markedly improved.

Figure 1:
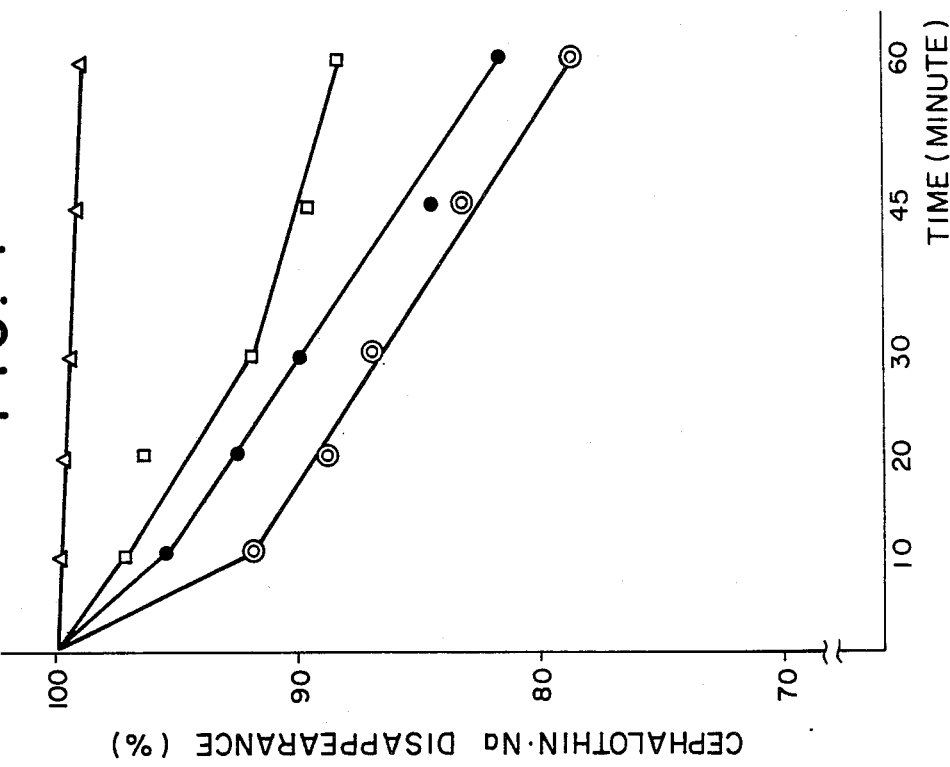

In the accompanying drawings,

FIG. 1 a disappearance curve of Cephalothine.Na versus osmotic pressure; and

FIG. 2 a curve of calcium concentration in serum when using Elcitonin as medicine.

According to the present invention, a preparation is provided which comprises a water-soluble substance at a concentration exhibiting an osmotic pressure higher than isotonic sodium chloride solution, a water-soluble compound having chelating activity and a medicine.

According to the present invention, there is also provided a preparation, which comprises a water-soluble macromolecular compound having chelating activity and a medicine.

A water-soluble substance useful in the present invention at a concentration exhibiting higher osmotic pressure than isotonic sodium chloride solution, is preferably one which is non-toxic and can exhibit high osmotic pressure with an amount as small as possible.

Typically useful compounds include water-soluble salts and water-soluble sugars.

The prepferred water soluble salt is sodium chloride since it is safe and readily controllable to provide a selected osmotic pressure, and is soluble in water rapidly at a high dissolving rate. Mannitol or glucose are preferred among water-soluble sugars. Generally speaking, water-soluble salts may include, for example, halides, sulfates, phosphates or carbonates of alkali metals such as sodium, potassium or lithium, more specifically sodium chloride, sodium sulfate, disodium hydrogen phosphate, sodium dihydrogen phosphate, sodium phosphate, sodium hydrogen carbonate, sodium carbonate, potassium chloride, potassium sulfate, potassium hydrogen phosphate, potassium carbonate, lithium chloride, etc. These salts may be adjusted to concentrations exhibiting higher tonicity than the osmotic pressure of isotonic sodium chloride solution. For example, in case of sodium chloride, it may generally be adjusted to a concentration of 1 W/W% or higher. The upper limit of the concentration is not particularly limited, but preferably the concentration is about 2 to 30 W/W%. As preferable water-soluble sugars, there may be employed monosaccharides or disaccharides frequently used for adjustment of osmotic pressure in pharmaceutical technology, including, for example, glucose, mannitol, sorbitol, xylitol, lactose, maltose and sucrose. Such a sugar may be used at a concentration with higher tonicity than isotonic sodium chloride solution, which is generally 0.25M or higher. Mixtures of these water-soluble substances may be employed for adjustment of osmotic pressure, which is preferably 1.5 to 6 times the osmotic pressure exhibited by isotonic sodium chloride solution.

A number of compounds having chelating action useful as abosrption promoters in this invention, they were investigated by adding to, for example, isotonic preparations for rectal application containing a medicine and then determining the increase or decrease of membrane absorption of the medicine. The mechanism of promotion effect has not so far been clarified, but it seems likely that membrane absorption mechanism may be changed through the chelating action and affinity to membrane possessed by these absorption promoters on the structures of cell membranes or the spaces between the epithelial cells thereby to promote absorption. This invention should not be limited by any theory of action of the chelating agent since the mechanism is not completely understood. It has been found however that it is sufficient to employ a water-soluble macromolecular compound having chelating action capable of bonding to at least calcium ions or magnesium ions. More specifically, as the chelating ligands for effective chelating action, there may be mentioned, for example, compounds containing acid groups such as carobxylic acid group, sulfonic acid group, phosphoric acid group, phenolic hydroxyl group, etc., hydroxyl group, imino group, carbonyl group, amino group, etc.

Further, as water-soluble macromolecular compounds having chelating action capable of bonding to at least calcium ions or magnesium ions, any water-soluble macromolecular having two or more chelating ligands may be used. Typical examples are water-soluble polysaccharide compounds, water-soluble cellulose derivatives, dextran derivatives, water-soluble starch derivatives, water-soluble synthetic polymers, water-soluble peptide compounds or water-soluble derivatives thereof having two or more chelating ligands. These compounds may also be esterified but not to the extent such that chelating activity is lost. These compounds may contain at least two of one or more kinds of chelating ligands selected from carobxylic acid groups, sulfonic acid groups, phosphoric acid groups, phenolic hydroxyl groups, hydroxyl groups, imino groups, carbonyl groups and amino groups, and they may either natural, semi-synthetic or synthetic products. Examples of these natural, semi-synthetic or synthetic water-soluble macromolecular compounds having chelating activity are enumerated below, but the present invention is not limited thereto.

Water-soluble polysaccharides containing uronic acid:
alginic acid, pectinic acid, chondroitin sulfate, hyaluronic acid, arabic acid;
Water-soluble cellulose related compounds:
carboxymethyl cellulose, carboxyethyl cellulose, carboxypropyl cellulose, cellulose acetate phthalate;
Water-soluble starch related compounds:
carboxymethyl starch, carboxyethyl starch;
Dextran related compounds:
carboxymethyl dextran, dextran sulfate;
Polypeptide compounds:
polyglutamic acid, poly-γ-carboxyglutamic acid, polyaspartic acid, polylysine, polyalginine and copolymers of these amino acids;
Water-soluble syntheric polymer compounds:
polyacrylic acid, polymethacrylic acid, methacrylic acid-acrylic acid copolymer, acrylamide-acrylic acid copolymer, polyphosphoric acid Further, these compounds or water-soluble base polymers exhibiting no detectable chelating activity may be bound with a chelating agent of low molecular weight having chelating activity to be converted to water-soluble macromolecular compounds having chelating activity as a whole.

In this case, the base polymer may be any one having water-solubility and may be exemplified by synthetic polymers such as polyvinyl alcohol, polyethylene oxide, etc. or various natural polymers. Preferably, a polymer having no toxic effects on living bodies is employed and such a polymer may have side chain functional groups for introduction of chelating ligands such as hydroxyl groups, carboxyl groups, amino groups or imino groups.

The polymer may have a molecular weight which is not particularly limited, so long as it is soluble in water or capable of forming hydrogels, but generally it is in the range of from 1000 to 1,000,000.

Typical non-limiting examples of such a water-soluble base polymer are set forth below.

Typical examples of water-soluble base polymers

Polysaccharides containing uronic acid:
chondroitin sulfate, heparin, arabic acid, pectin, gum tragacanth, tragacanthic acid, pectinic acid;
Other polysaccharides:
carrageenan, β-gulcan, galactomannan, konjakmannan, galactan, fucan, inulin, levan;
Cellulose related compounds:
hydroxyethyl cellulose, hydroxypropyl cellulose, cellulose, methyl cellulose, ethyl cellulose, hydroxypropylmethyl cellulose, agarose;
Starch related compounds:
soluble starch, phosphoric acid starch, acetyl starch, hydroxyethyl starch, dextrin, amylose, amylopectin;
Dextran related compoudns:
dextran, diethylaminoethyl dextran, aminoethyl dextran;
Polypeptides:
gelatin, casein, albumin, globulin;
Synthetic polymers:
polyethylene glycol, polyvinyl alcohol, polyethylene oxide, vinyl acetate-maleic acid copolymer, vinyl acetate-crotonic acid copolymer, vinyl acetate-acrylic acid copolymer, polyvinyl aocohol-maleric acid copolymer, polyacrylamide, polyvinylacetal diethylaminoacetate, 2-methyl-5-vinylpyridine/methyl acrylate/methacrylic acid copolymer.

As chelating agent to be incorporated into these water-soluble base polymers, there may be used a compound capable of forming a chelate with calcium ions or magnesium ions which can be introduced into the polymer side chain without loss of chelate forming activity.

A typically useful chelating compound for use in this invention may contain any of three kinds of ligand or functional groups. The chelaters may be those which (I) contain a proton as chelate forming functional group to be substituted by said metal ion (e.g. hydroxyl group, carboxyl group, imino group, etc.), or (II) a ligand capable of coordination bonding to the metal ion (e.g. carbonyl group, amino group, etc.) and a functional group. The functional group for bonding the chelater to the polymer as a side chain through formation of bondings such as amide bonding, ester bonding or ether bonding by reaction with the polymer should be capable of forming such bonds. These include, for example the amino group, carboxyl group, hydroxyl group, halogen, etc). The compound should be one having a structure such that the chelate forming ligands (I) and (II) are separated by a link having 1 to 2 carbon atoms or that (I) and (II) are separated from (III), which is the link with a polymer, by an organic group having 1 to 10 carbon atoms such as an aliphatic group or an aromatic group.

Typical examples of such compounds are enumerated below, but the present invention is not limited thereto.
Aliphatic polycarboxylic acid compounds:

oxalic acid, malonic acid, succinic acid, maleic acid, fumaric acid, aconitic acid, pimellic acid, sebacic acid, allylmalonic acid, ethylmalonic acid;

Aliphatic oxycarboxylic acid compounds:

citric acid, malic acid, glyceric acid, tartaric acid, mevaloic acid, oxyglutaric acid;

Aliphatic keto-polycarboxylic acid compounds:

oxaloacetic acid, $\alpha$-ketoglutaric acid, $\beta$-ketoglutaric acid, $\alpha$-ketomalonic acid;

Uronic acid compounds:

glucuronic acid, galacturonic acid, mannuronic acid;

Amino acid compoudns:

aspartic acid, glutamic acid, glycine, alanine, lysine, hystidine, alginine, cysteine, $\epsilon$-aminocaproic acid, phenylalanine, phenylglycine, p-hydroxyphenylglycine, p-aminophenylalanine, $\gamma$-carboxyglutamic acid;

Aminopolycarboxylic acid compounds:

iminodiacetic acid, hydroxyethyliminodiacetic acid, ethylenediaminediacetic acid, ethylenediaminetetraacetic acid, transcyclohexanediaminetetraacetic acid, diethylenediaminepentaacetic acid, $\beta$-alaninediacetic acid, diaminopimellic acid;

Aromatic carboxylic acid compounds:

phthalic acid, terephthalic acid, homophthalic acid, phenylsuccinic acid, phenylmalonic acid, oxanylic acid-o-carboxylic acid, anithralininoacetic acid, 2,4-dihydroxybenzoic acid, p-aminosalicylic acid, phthalylglutamic acid, kynurenine;

Aliphatic and aromatic sulfonic acid compounds:

1,2-hydroxybenzene-3,5-disulfonic acid, 4-aminophenol-2-sulfonic acid, cysteic acid;

Phosphoric acid compounds:

2-phosphoglyceric acid, glycero-3-phosphoric acid, glucose-1,6-diphosphoric acid, fructose-1,6-diphosphoric acid.

For incorporation of such a chelating agent into a water-soluble base polymer, the chelating agent and the incorporation method to be employed are suitably selected depending on the side chains of the water-soluble base polymer employed, and the bonding formed as the result of the reaction is also determined by their conbination, as described in detail in Japanese Patent Publication No. 16979/1979 (U.S. Pat. No. 4,024,073).

The effect of promoting absorption of a medicine by the water-soluble macromolecular compound having chelating activity obtained according to the present invention was examined by use of, for example, an Elcitonin preparation containing the lysine-dextran T-150 prepared according to Example 1 disclosed in Japanese Patent Publication No. 16979/1979 (U.S. Pat. No. 4,024,073) by intrarectal injection in vivo into rats and measuring decrease in calcium concentration in serum, whereby it was found that said preparation exhibited significant absorption promoting effect as compared with Control using no lysine-dextran T-150. These macromolecular adsorption are generally used in the formed alkali metal salts such as sodium salts or potassium salts, or ammonium salts.

The water-soluble low molecular compound and the macromolecular compound having chelating action or the water-soluble polymer having incorporated a chelating agent in the present invention is used as a membrane absorption promoter. These absorption promoters may be employed in amounts of 0.05 W/W% or more, generally in the range of from 0.1 to 50 W/W%, preferably from 1.0 to 30 W/W%. As the vehicle to be employed for preparation of a suppository containing the above absorption promoter, a medicine and preferably a water-soluble salt to be added for increase of tonicity, there may suitably be selected one from oily vehicles and water-soluble vehicles conventionally used in preparation of suppositories or rectal injections, and a surfactant may also be added if desired. Two or more promoters may be used together.

Typically useful oil or water-soluble vehicles, described in "The Theory and Practice of Industrial Pharmacy", p. 245 to 269 (1976).

Any of a wide variety of therapeutic agents may be employed in the practice of this invention. These include, for example, water-soluble therapeutic agents which are excellently soluble in water, such as water-soluble medicines with a partition coefficient of up to 50 in chloroform/water or medicines readily dissociated to ions. For example, there may be included various medicines such as hypnotics, tranquilizers, antiepileptics, antipyretics, analgesics, antidepressants, muscle relaxants, anti-inflammatory agents, antiallergic agents, immunosuppressants, antirheumatics, vasodilators, anthemorragics, antihypertensives, antibiotics, antibacterial agents, urinary tract sterilizers, antitumor agents, vitamins, hormones and galenicals. More specifically, typical examples are penicillin type antibiotics such as ampicillin, hetacillin, amoxicillin, cyclacillin, cloxacillin, dicloxacillin, oxacillin, carindacillin, sulbenicillin, piperacillin, apalcillin, methicillin, etc. or combined drugs of ampicillin or amoxicillin with oxacillin, cloxacillin, floxacillin or dicloxacillin; cephalosporin type antibiotics such as cephalothin, cephazolin, cephaloridine, cephacetorile, cefoxitin, cefadoxil, cefatrizine, cephaloglycin, cephalexin, cephapirin, cehphaclor, ceftezol, cefuroxime, cefsulodin, cefmetazole, etc. and non-toxic salts thereof such as alkali metal salts (e.g. sodium salts or potassium salts), ammonium salts or benzylamine salts. In addition, there may also be mentioned tetracycline type antibiotics such as doxycycline, oxycycline, etc; aminosaccharide type antibiotics such as kanamycin, sisomicin, amikacin, tobramycin, netromycin, gentamycin, etc; peptide type antibiotics such as tuberactinomycin N, actinomycin, etc. or non-toxic salts thereof; further peptide hormones such as insulin, somatostatin, calcitonin, angiotensin, kallikrein, secretin, gastrisin, parathyroid hormone, etc; and other medicines such as barbital, theophylline, aspirin, mizoribine (bredinin), 5-fluorouracil, methotrexate, L-dopa, etc. The medicine may be employed in an amount, which may suitably be selected and designed. For example, in case of antibiotics such as $\beta$-lactam antibiotics, 20 to 500 mg activity, generally 100 to 300 mg activity, or in case of peptide hormones such as insulin, 1 to 500 units may be contained per gram of preparation. In general, the medicine may preferably be used in finely divided forms with 1 to 50$\mu$ diameters or as an aqueous solution.

The step of forming preparations may be performed according to conventional methods for production of preparations in general such as rectal suppository, urethral suppository or vaginal suppository, ointments or creams. For example, the absorption promoter selected, a water-soluble substance in an amount exhibiting higher osmotic pressure than isotonic sodium chloride solution and a medicine are added to a vehicle, optionally in combination with a surfactant, and these components are thoroughly mixed to provide the desired preparations.

Further, in production of these preparation, there may also be added preservatives such as methyl- or propyl-p-oxybenzoate, colorants, aromas and stabilizers.

The present invention is further illustrated in detail referring to the following Examples. The examples do not limit the invention since, as will be clear from the above, any of a wide variety of medicines, hypertonicators and absorption promoters may be selected and combined in addition to those shown in Examples.

EXAMPLE 1

To a 0.1 W/W% Cephalothin.Na solution, there was added 0.1 W/W% pectinic acid and mannitol was added at various levels to prepare an isotonic solution, a two-fold tonic solution and a four-fold tonic solution, respectively. As Control, an isotonic solution without use of pectinic acid was also prepared. Subsequently, these samples were administered to Wistar-strain rats as shown below and quantities of Cephalothin disappeared by absorption were measured.

In the experiment, Wistar-strain male rats, weighing 250 to 300 g, were narcotized with pentobarbital (50 mg/kg) and thereafter subjected to hypoabdominal incision for a first cannulation at a position about 1.5 cm from the anus and also another cannulation at a position 5 cm above the first cannulation. Subsequently, the rectum was internally washed with about 20 ml of isotonic sodium chloride solution kept at 38° C., and each sample was circulated at a flow rate of 2 ml/minute for 5 minutes to make the concentration in the system constant. Then, 6 ml of each sample was circulated at a flow rate of 2 ml/minute, and samples each of 0.05 ml were collected at intervals of 10 minutes. Each sample was diluted and the quantity of Cephalothin disappeared was determined by UV-spectrophotometer or high-speed liquid chromatography.

The results are shown in FIG. 1, wherein △—△ indicates the disappearance curve of Cephalothin in case of Control using no pectinic acid, □—□ disappearance curve in case of isotonic solution using pectinic acid, ●—● that of two-fold tonic solution using pectinic acid and ⊙—⊙ that of four-fold tonic solution using pectinic acid.

As will be apparent from FIG. 1, use of pectinic acid improves remarkably absorption of Cephalothin and further improvement is brought about by using in combination pectinic acid under hyper tonic conditions.

EXAMPLE 2

In place of pectinic acid in the above Example 1, there were employed sodium alginate, sodium carboxymethyl cellulose, sodium polyacrylate, chorodroitin sulfate, sodium polyaspartate and sodium polyglutamate each at a concentration of 0.1 W/W%, and each solution was adjusted with sodium chloride to various tonicities, namely isotonic (×1), two-fold tonic (×2) and four-fold tonic (×4) solutions. As the result, the quantities of Cephalothin disappeared at the time of sampling 60 minutes after circulation were found as shown in Table 1.

TABLE 1

| Absorption promoter | Osmotic pressure (%) | | |
|---|---|---|---|
| | X 1 | X 2 | X 4 |
| Sodium alginate | 6.3 | 10.2 | 22.4 |
| Sodium carboxymethyl cellulose | 7.1 | 10.2 | 18.7 |
| Sodium polyacrylate | 6.7 | — | 14.6 |
| Chondroitin sulfate | 4.0 | 6.7 | 11.5 |
| Sodium polyaspartate | 8.4 | 11.5 | 20.4 |

TABLE 1-continued

| Absorption promoter | Osmotic pressure (%) | | |
|---|---|---|---|
| | X 1 | X 2 | X 4 |
| Sodium polyglutamate | 7.9 | 15.0 | 33.6 |
| No addition | 1.2 | 1.6 | 3.1 |

EXAMPLE 3

Using absorption promoters, prepared as described hereinafter in Reference examples, of aspartic acid-carboxymethyl cellulose, iminodiacetic acid-alginic acid, iminodiacetic acid-carboxymethyl starch, glycine-starch, glycine-polyacrylic acid, ethylenediaminetetraacetic acid-dextran and hydrochelidonic acid-albumin, various samples of preparations were obtained with adjustment of tonicity to isotonic (×1), two-fold tonic (×2) and four-fold tonic (×4). For each sample, the quantity of Cephalotin disappeared was determined similarly as in Example 1. As the result, the quantities of Cephalothin disappeared at the time of sampling 60 minutes after circulation were found as shown in Table 2.

TABLE 2

| Absorption promoter | Osmotic pressure (%) | | |
|---|---|---|---|
| | X 1 | X 2 | X 4 |
| Aspartic acid-carboxymethyl cellulose | 7.0 | 10.4 | 22.6 |
| Iminodiacetic acid-alginic acid | 7.2 | 10.5 | 24.6 |
| Iminodiacetic acid-carboxymethyl starch | 5.2 | 9.8 | 18.8 |
| Glycine-starch | 5.1 | 8.8 | 11.9 |
| Glycine-polyacrylic acid | 6.9 | 10.1 | 17.0 |
| Ethylenediaminetetraacetic acid-dextran | 5.8 | 9.2 | 16.7 |
| Hydrochelidonic acid-albumin | 4.2 | — | 9.5 |

EXAMPLE 4

Elcitonin (Asu$^{1.7}$-eel calcitonin) (100 units and 10 units), sodium alginate (50 mg) and sodium chloride (50 mg) were dissolved in 1 ml of distilled water. Each solution (0.1 ml) was administered intrarectally to SD-strain male rats (four weeks of age) and calcium concentrations in serum were measured 30 minutes, 60 minutes and 90 minutes after administration by atomic absorption method. As Control, there was used a solution containing no sodium alginate (adjusted to 100 units of Elcitonin). Further, similar test was conducted by use of 50 mg of pectinic acid in place of sodium alginate.

The results are shown in FIG. 2, wherein x—x indicates calcium concentrations in serum in case of Control, ○—○ those in case of a solution containing sodium alginate and sodium chloride adjusted to 100 units of Elcitonin, △—△ those in case of a solution containing pectinic acid and sodium chloride at 100 units of Elcitonin, ●—● those in case of a solution containing sodium alginate and sodium chloride at 10 units of Elcitonin, ▲—▲ those in case of a solution containing pectinic acid and sodium chloride at 10 units of Elcitonin, respectively.

EXAMPLE 5

Cephalothin.Na (200 g Potency), sodium alginate (50 g) and sodium chloride (50 g), each being pulverized, were mixed and the resulting mixture was dissolved in 2% gelatin solution to a volume of one liter, which was then filled into injection cylinders in aliquots each of 1 ml to provide intrarectal injection preparations.

EXAMPLE 6

Gentamycin (100 g Potency), sodium pectinate (50 g) and mannitol (250 g), each being pulverized, were mixed and the mixture was homogeneously dispersed in 5% gelatin solution to a volume of one liter, which was then filled into injection cylinders in aliquots each of 1 ml to provide intrarectal injection preparations.

EXAMPLE 7

One thousand units of Elcitonin, 50 g of sodium pectinate and 250 g of mannitol were each pulverized and mixed together. The resulting mixture was dispersed homogeneously in 5% gelatin solution to a volume of one liter, which was then filled into injection cylinders in aliquots each of 1 ml to provide injection preparations for vaginal suppository.

EXAMPLE 8

One thousand units of Elcitonin, 50 g of sodium pectinate and 250 g of mannitol were dispersed homogeneously in Witepsol H-15 molten by heating to an amount of 1 kg, which was then filled in suppository containers in aliquots each of 1 g to provide rectal suppositories.

EXAMPLE 9

One thousand units of Elcitonin, 50 g of sodium alginate and 5 g of sodium chloride were dissolved in 100 ml of distilled water and the solution was added to Witepsol H-5 containing 1% Span 60 (produced by Kao-Atlas Co.) to an amount of 500 g, followed further by homogeneous emulsifying. The emulsion was filled in suppository containers in aliquots each of 1 g to provide rectal suppositories.

EXAMPLE 10

Cefoxitin.Na (100 g Potency), sodium alginate (50 g) and sodium chloride (50 g) each being pulverized were mixed and dispersed in Witepsol H-5 molten by heating to an amount of 1 kg, which was then filled in suppository containers in aliquots each of 1 g to provide suppositories.

EXAMPLE 11

Example 10 was repeated except that Cephazolin.Na (200 g Potency) was employed in place of Cefoxitin.Na to obtain suppositories.

REFERENCE EXAMPLE 1

Ten grams of commercially available carboxymethyl cellulose.Na were dissolved in 400 ml of 17.5% sodium hydroxide solution and subjected to mercerization at 3° to 5° C. under nitrogen atmosphere. The product was diluted to 2 liters with deionized water and then adjusted to pH 11 with hydrochloric acid. Then, 100 ml of an aqueous solution containing 5 g of bromocyan was added to the solution and the reaction was carried out at room temperature for 5 minutes. After the reaction was over, pieces of ice were added to cool the mixture to lower than 5° C., whereupon an aqueous solution of pH 10 containing 150 mmol of aspartic acid and 1 mmol of ethylenediaminetetraacetic acid was added and the reaction was carried out at 5° C. overnight. After the reaction, the reaction mixture was neutralized with 6N-hydrochloric acid, concentrated under reduced pressure, further adjusted to pH 10.5 with 5N-sodium hydroxide solution to dissolve insolubles formed during concentration. Then, the mixture was dialyzed against water and further against 0.01N hydrochloric acid, followed by lyophilization to obtain 8.5 g of aspartic acid-carboxymethyl cellulose.

REFERENCE EXAMPLE 2

Sodium alginate (1.5 g) was dissolved in 100 ml of distilled water, adjusted to pH 8.0 and 10 mmol of hydroxysuccinimide was added thereto, and the reaction was carried at 5° C. for 60 minutes to obtain an activated ester. After the reaction, 10 mmol of aminodiacetic acid was added to effect the reaction. Then, the reaction mixture was charged to Sephadex G-200 and eluted with 10 mM phosphate buffer (pH 6.5). The eluted fractions were recovered and lyophilized to obtain 1.0 g of iminodiacetic acid-alignic acid.

REFERENCE EXAMPLE 3

Reference example 2 was repeated except that 1.5 g of carboxymethyl starch.Na was employed in place of sodium alginate to obtain 0.8 g of iminodiacetic acid-carboxymethyl starch.

REFERENCE EXAMPLE 4

Using a commercially available soluble starch, after activation similarly as in Reference example 1, it was reacted with glycine to obtain 7.6 g of glycine-starch.

REFERENCE EXAMPLE 5

After a commercially available sodium polyacrylate was subjected to activated esterification similarly as in Reference example 2, the reaction product was allowed to react with glycine to obtain 8.2 g of glycine-polyacrylic acid.

REFERENCE EXAMPLE 6

A mixture of ethylenediaminetetraacetic acid, acetic acid anhydride and pyridine was subjected to the reaction at 65° C. for 24 hours to obtain dihydride of ethylenediaminetetraacetic acid. The product was then added into dimethylformamide and further dextran was added to carry out the reaction. Distilled water was added to the reaction mixture, and then ethylenediaminedextran was obtained by filteration.

REFERENCE EXAMPLE 7

After hydrochelidonic acid was converted to an active ester similarly as in Reference example 6, the ester was reacted with albumin to obtain hydrochelidonic acid-alubumin.

What we claim is:

1. A therapeutic composition for rectal or vaginal administration having excellent absorption properties and containing a therapeutically effective amount of a water soluble therapeutic agent having a partition coefficient of up to 50 in chloroform/water, and additionally containing from 0.1 to 50 w/w% of a water soluble chelating agent selected from the group consisting of polysaccharide compounds, cellulose compounds, starch compounds, dextrose compounds, polypeptides and synthetic polymers, said agent being capable of chelating calcium or magnesium ions, having a molecular weight of from 1000 to 1,000,000, and containing at least two chelating ligands selected from the group consisting of carboxylic, sulfonic, phosphoric, phenolic, hydroxyl, carbonyl, imino and amino groups.

2. A therapeutic composition of claim 1 wherein the chelating agent is selected from the group consisting alginic acid, pectinic acid chondroitin sulfate hyaluronic acid, arabic acid; carboxymethyl cellulose, carboxyethyl cellulose, carboxypropyl cellulose, cellulose acetate phthalate; carboxymethyl starch, carboxyethyl starch; carboxymethyl dextran, dextran sulfate; polyglutamic acid, poly-γ-carboxyglutamic acid, polyaspartic acid, polylysine, polyarginine and copolymers of these amino acids; polyacrylic acid, polymethacrylic acid, methacrylic acid-acrylic acid copolymer, acrylamide-acrylic acid copolymer polyphosphoric acid.

3. A therapeutic composition of claim 1 wherein the chelating agent is selected from the group consisting chondroitin sulfate heparin, arabic acid, pectin, gum tragacanth, tragacanthic acid, pectinic acid; carrageenan, -glucan galactomammam, konjakmannan, galactan, fucan, inulin, levan; hydroxyethyl cellulose, hydroxypropyl cellulose, cellulose, methyl cellulose, ethyl cellulose, hydroxypropylmethyl cellulose, agarose; soluble starch phosphoric acid starch, cetyl starch, hydroxyethyl starch, dextrin, anylose, amylopectin; dextran, diethylaminoethyl dextran, aminoethyl dextran; gelatin, casein, albumin, globulin; polyethylene glycol, polyvinyl alcohol, polyethylene oxide, vinyl acetate-maleic acid copolymer, vinyl acetate-crotonic acid copolymer, vinyl acetate-acrylic acid copolymer, polyvinyl alcohol-maleic acid copolymer, polyacrylamide, polyvinylacetal diethylaminoacetate, 2-methyl-5-vinylpyridine/methyl acrylate/methacrylic acid copolymer.

4. A therapeutic composition of claim 1 wherein the therapeutic agent is calcitonin.

5. A therapeutic composition of claim 1 wherein the therapeutic agent is an antibiotic.

6. A therapeutic composition of claim 5 wherein the antibiotic is selected from the group consisting of β-lactam antibiotics, tetracycline antibiotics, aminosugar antibiotics and peptide antibiotics.

7. A therapeutic composition of claim 1 wherein the therapetuic agent is a hormone.

8. A therapeutic composition of claim 7 wherein the hormone is peptide hormone.

9. A therapeutic composition for rectal or vaginal administration having excellent absorption properties containing a therapeutically effective amount of a water soluble therapeutic agent having a partition coefficient of up to 50 in chloroform/water and additionally containing:

1. from 0.1 to 50 w/w% of a water soluble chelating agent selected from the group consisting of polysaccharide compounds, cellulose compounds, starch compounds, dextrose compounds polypeptic compounds and synthetic polymers, said agent being capable of chelating calcium or magnesium ions, having a molecular weight of from 1000 to 1,000,000 and containing at least two chelating ligands selected from the group consisting carboxylic, sulfonic, phosphoric, phenolic, hydroxyl, carbonyl, imino and amino groups;

2. from 0.1 to 50 w/w% of a water soluble solute elected from the group consisting of halides, sulfates, phosphates and carbonates of alkali metals, and mono-and diaccharides, the total concentration of solute being sufficient so that the composition when dissolved in a fixed amount of aqueous media exerts an osmotic pressure 1.5 to 6 times the osmotic pressure of isotonic sodium chloride solution.

10. A therapeutic composition of claim 9 wherein the water soluble chelating agent is selected from the group consisting alginic acid, pectinic acid, chondroitin sulfate, hyaluronic acid, arabic acid; carboxymethyl cellulose, carboxyethyl cellulose, carboxypropyl cellulose, cellulose acetate phthalate; carboxymethyl starch, carboxyethyl starch; carboxymethyl dextran, dextran sulfate; polyglutamic acid, poly-γ-carboxyglutamic acid, polyaspartic acid, polylysine, polyalginine and copolymers of these amino acids; polyacrylic acid, polymethacrylic acid, methacrylic acid-acrylic acid copolymer, acrylamideacrylic acid copolymer, polyphosphoric acid.

11. A therapeutic composition of claim 9 wherein the water soluble chelating agent is selected from the group consisting chondroitin sulfate, heparin arabic acid, pectin, gum tragacanth, tragacanthic acid, pectinic acid; carrageenan, β-glucan, galactomanna konjakmannan, galactan, fucan, unulin, levan; hydroxyethyl cellulose, hydroxypropyl cellulose, cellulose, methyl cellulose, ethyl cellulose, hydroxypropylmethyl cellulose, agarose; soluble starch, phosphoric acid starch, acetyl starch, hydroxyethyl starch, dextrin, amylose, amylopectin; dextran, diethylaminoethyl dextran, aminoethyl dextran; gelatin, casein, albumin, globulin; polyethylene glycol, polyvinyl alcohol, polyethylene oxide, vinyl acetate-maleic acid copolymer, vinyl acetate-crotonic acid copolymer, vinyl acetate-acrylic acid copolymer, polyvinyl alcohol-maleric acid copolymer, polyacrylamide, polyvinylacetal diethylaminoacetate, 2-methyl-5-vinylpyridine/methyl acrylate/methacrylic acid copolymer.

12. A therapeutic composition of claim 9 wherein the therapeutic agent is calcitonin.

13. A therapeutic composition of claim 9 wherein the water soluble therapeutic agent is an antibiotic.

14. A therapeutic composition of claim 9 wherein the antibiotic is selected from the group consisting of β-lactam antibiotics, tetracycline antibiotics, aminosugar antibiotics and peptide antibiotics.

15. A therapeutic composition of claim 9 wherein the water soluble therapeutic agent is a hormone.

16. A therapeutic vagina composition of claim 15 wherein the hormone is a peptide hormone.

* * * * *